(12) United States Patent
Chenevier et al.

(10) Patent No.: US 7,718,194 B2
(45) Date of Patent: May 18, 2010

(54) COATED PARTICLES WITH PROLONGED RELEASE AND TABLETS CONTAINING SAME

(75) Inventors: Phillippe Chenevier, Montreal (CA); Dominique Marechal, Laval (CA)

(73) Assignee: Ethypharm, Houdan (FR)

( * ) Notice: Subject to any disclaimer, the term of this patent is extended or adjusted under 35 U.S.C. 154(b) by 695 days.

(21) Appl. No.: 10/512,220

(22) PCT Filed: Apr. 23, 2003

(86) PCT No.: PCT/FR03/01284

§ 371 (c)(1),
(2), (4) Date: Oct. 22, 2004

(87) PCT Pub. No.: WO03/090724

PCT Pub. Date: Nov. 6, 2003

(65) Prior Publication Data

US 2005/0152976 A1 Jul. 14, 2005

(30) Foreign Application Priority Data

Apr. 23, 2002 (FR) .................................. 02 05077

(51) Int. Cl.
*A61K 9/16* (2006.01)
*A61K 9/20* (2006.01)
(52) U.S. Cl. .................... 424/490; 424/464; 424/493; 424/494; 424/495
(58) Field of Classification Search .................. None
See application file for complete search history.

(56) References Cited

U.S. PATENT DOCUMENTS 5,674,529 A * 10/1997 Marder et al. ............... 424/468
5,718,923 A * 2/1998 Matsuda et al. ............. 424/502
6,077,544 A * 6/2000 Debregeas et al. .......... 424/497
6,132,770 A * 10/2000 Lundberg .................... 424/466
6,299,904 B1 * 10/2001 Shimizu et al. ............. 424/464
2004/0006111 A1 * 1/2004 Widder et al. ............... 514/338

FOREIGN PATENT DOCUMENTS

| GB | 1598458 | 9/1981 |
| WO | 9639127 A1 | 12/1996 |
| WO | 9944580 A1 | 9/1999 |

OTHER PUBLICATIONS

"Polyethylene Glycols"; Sheftel, VO. Indirect Food Additives and Polymers: Migratation and Toxicology. Lewis 2000 pp. 1114-1116.*
Beckert et al., "Compression of enteric-coated pellets to disintegrating tablets", International Journal of Pharmaceutics 143 (1996), pp. 13-23.
Bodmeier, "Tableting of coated pellets", European Journal of Pharmaceutics and Biopharmaceutics 43 (1997), pp. 1-8.
Hutchings et al., "Studies of the mechanical properties of free films prepared using an ethylcellulose pseudolatex coating system", International Journal of Pharmaceutics 104 (1994), pp. 203-213.
Van Bommel et al., "Effects of Additives on the Physico-chemical Properties of Sprayed Ethylcellulose Films", Acta Pharm. Technol. 35 (4) (1989), pp. 232-237.
International Search Report for PCT/FR2003/01284.

* cited by examiner

*Primary Examiner*—S. Tran
(74) *Attorney, Agent, or Firm*—Caesar, Rivise, Bernstein, Cohen & Pokotilow, Ltd.

(57) ABSTRACT

The invention concerns coated particles with prolonged release, a method for preparing same and multiparticulate tablets comprising said coated particles.

23 Claims, No Drawings

COATED PARTICLES WITH PROLONGED RELEASE AND TABLETS CONTAINING SAME

The invention relates to coated particles and more specifically to sustained-release coated granules or granulates, to a process for preparing them and to multiparticulate tablets comprising said coated particles.

Sustained-release multiparticulate forms are well known in the prior art.

These forms exist in particular in unit forms such as gel capsules or multiparticulate tablets.

The term "multiparticulate tablet" means a tablet comprising, firstly, particles containing at least one active principle, which are individually coated with a polymer film that modifies the release of the active principle over a period that can range from 8 to 24 hours, and, secondly, tabletting excipients.

The coated particles are first mixed with the tabletting excipients, the mixture then being compressed so as to give a homogeneous unit form. During the compression step, the polymer coating experiences large stresses, which are such that cracks or breaks may appear, resulting in loss and immediate availability of all of the active principle.

The polymer film should thus be flexible enough and deformable enough to withstand compression.

To evaluate the mechanical properties and characteristics of the polymer film, parameters such as the breaking strength or the percentage of elongation may be used. These mechanical characteristics may be determined by the methods described in standards DIN 53455 and ISO/RI 184.

Acrylic polymers are a family of polymers with deformation properties that allow the preparation of multiparticulate tablets.

In Patent Application EP 1 032 374, the Applicant describes spheroids comprising, in the core or as a layer, a thermoplastic excipient with a pasty to semi-solid consistency at 20° C., and a flexible and deformable film whose percentage of elongation is greater than or equal to 50%, and which consists of a neutral copolymer of acrylic acid esters, for example the product sold under the brand name Eudragit® NE30D, the percentage of elongation of which is 600% and the compressive strength of which is 8 N m².

Polymers that have mediocre elongation or compressive strength parameters do not normally absorb the mechanical stresses associated with tabletting (International Journal of Pharmaceutics, 143, 13-23 (1996)).

Numerous publications describe cellulose-based polymers as being brittle and inelastic. This is the case, for example, for ethylcellulose, the elongation capacity of which is usually less than 15%, which makes it difficult for it to be used as a coating agent for particles intended to be compressed (Eur. J. Pharm. Biopharm., 43, 1-8 (1997)).

Studies on ethylcellulose-based free films show that the addition of plasticizers or of soluble agents to the coating film, and the use of a maturation step under certain temperature and humidity conditions (Int. J. Pharm. 104, 203-213, (1994), Acta Pharm. Technol. 35(4), 232-237, (1989)) can make it possible to improve the properties of films based on cellulose derivatives.

However, this improvement is insufficient. Moreover, the release profile of the active principle is directly influenced by the composition of the coating film.

It would be particularly advantageous to have available means for making them systematically usable for the constitution of coating films, without modifying their composition or having an influence on their active principle release profile.

However, to its credit, the Applicant has now found that this aim can be achieved and that it has become possible to obtain sustained-release coated particles with a coating consisting of at least one cellulose-based polymer such that the release profile of a multiparticulate tablet based on these particles is identical to that of the coated particles before tabletting, the two release profiles being determined under similar working conditions (dissolution medium, apparatus, method), since said particles are given a protective coating based on at least one thermoplastic agent with a melting point of from 25 to 100° C. applied over the coating based on cellulose-based polymer.

It is considered that two release profiles are similar when the variation between the means of the values measured for each of the profiles at each sampling time is less than or equal to plus or minus 15% and preferably plus or minus 10%, i.e., in the present case, between the mean value obtained for the coated particles before tabletting and that obtained for the multiparticulate tablet based on said particles.

If the variation under consideration is greater than 15%, it is considered that the release profile is significantly modified.

It follows therefrom that the sustained-release coated particles in accordance with the invention, which comprise a core comprising an active principle and at least one binder, and a coating film based on at least one cellulose-based polymer, alone or as a mixture with a plasticizer, are characterized in that they comprise a protective coating based on at least one thermoplastic agent with a melting point of from about 25° C. to about 100° C. and which is applied to the coating film based on at least one cellulose-based polymer.

The particles in accordance with the invention consist of granules or granulates, depending on the process for obtaining the active core.

The granulates are obtained by dry or wet granulation and the granules by mounting the active principle on a neutral support.

The core of the particle comprises at least one active principle chosen from those of the group comprising gastrointestinal sedatives, antacids, analgesics, antiinflammatories, coronary vasodilators, peripheral and cerebral vasodilators, antiinfectives, antibiotics, antiviral agents, antiparasitic agents, anticancer agents, anxiolytics, neuroleptics, central nervous system stimulants, antidepressants, antihistamines, antidiarrheal agents, laxatives, dietary supplements, immunodepressants, hypocholesterolemiants, hormones, enzymes, antispasmodics, antianginal agents, medicinal products that affect the heart rate, medicinal products used in the treatment of arterial hypertension, antimigraine agents, medicinal products that affect blood clotting, antiepileptics, muscle relaxants, medicinal products used in the treatment of diabetes, medicinal products used in the treatment of thyroid dysfunctions, diuretics, anorexigenic agents, antiasthmatics, expectorants, antitussive agents, mucoregulators, decongestants, hypnotics, antinausea agents, hematopoietic agents, uricosuric agents, plant extracts and contrast agents.

This active principle, initially in the form of powder or microcrystals, is used in dry form for the preparation of granulates, and in the form of a solution or a suspension in an aqueous or organic solvent for mounting on neutral supports.

Advantageously, the cores comprise a binder for binding the powder or the microcrystals of active principle and the other possible constituents, so as to give particles of a size sufficient to facilitate the coating operation.

The binder may be chosen from the group especially comprising cellulose-based polymers, acrylic polymers, povidones, copovidones, polyvinyl alcohols, alginic acid, sodium alginate, starch, pregelatinized starch, sugars and derivatives thereof, guar gum and polyethylene glycols, and mixtures thereof.

Among the cellulose-based polymers that will advantageously be chosen are ethylcellulose, hydroxypropylcellulose and hydroxypropylmethylcellulose, alone or as a mixture.

Among the acrylic polymers that are advantageously chosen are ammoniomethacrylate copolymer, acrylic and methacrylic acid polymers and copolymers, polyacrylates and polymethacrylates, used alone or as a mixture.

The binder is present in proportions that may be up to 15% by weight and preferably up to 10% by weight relative to the weight of the uncoated particles.

The core optionally comprises a diluent and an antistatic agent.

The diluent may be chosen from the group especially comprising cellulose-based derivatives and preferably microcrystalline cellulose, starches alone, lactose and polyols, and preferentially mannitol.

The core may also be a neutral support consisting of a mixture of starch and sucrose, or alternatively microcrystalline cellulose.

The diluent is present in proportions that may be up to 95% by weight and preferably up to 50% by weight relative to the weight of the uncoated particles. Its role is to increase the total mass of particles to be coated and to obtain a population of particles of homogeneous size.

The antistatic agent may be chosen from the group comprising colloidal silica, especially the product sold under the brand name Aerosil®, and preferentially precipitated silica, especially the product sold under the name Syloid® FP244, and micronized or nonmicronized talc, and mixtures thereof.

The antistatic agent is present in proportions that may be up to 10% by weight and preferably up to 3% by weight relative to the weight of the uncoated particles.

It improves the fluidization of the material during the use of a fluidized air bed, in particular in the case of powder granulation.

The cores comprising the active principle are then coated with a first coating composition.

The coating film thus obtained allows the sustained release of the active principle.

This coating film consists of at least one cellulose-based polymer, alone or as a mixture with a plasticizer.

Ethylcellulose is preferably chosen among cellulose-based polymers.

This coating film is applied by spraying a solution, a suspension or a colloidal dispersion of this polymer in a solvent, to form a continuous film that covers all of the surface of each particle, irrespective of the surface state of said particle, in an amount sufficient to allow the sustained release of the active principle over a period that may range from 8 to 24 hours.

The coating polymer is present in proportions that may be up to 50% and preferably up to 20%, calculated as weight gain relative to the mass of cores to be coated.

The solvent chosen to spray the cellulose-based polymer may be water, an organic solvent, such as ethanol, isopropanol or acetone, or a mixture of solvents.

In this case, the polymer is in the form of a solution, suspension or dispersion, in the solvent or mixture of solvents. It is preferably in the form of a solution in an organic solvent, preferably in isopropanol.

The coating composition also optionally comprises a pore-forming agent, a plasticizer, a surfactant, an antistatic agent or a lubricant.

The pore-forming agent can modify the release of the active principle, and in particular can accelerate it.

This agent should be soluble in media with a pH of less than or equal to 5. It may be chosen, for example, from sugars, polyols, acrylic or methacrylic acid polymers or copolymers, hydroxylated cellulose derivatives, povidones and polyvinyl alcohols.

The plasticizer is chosen from the group comprising triethyl citrate, acetyltributyl citrate, triacetin, tributyl citrate, diethyl phthalate, polyethylene glycols, polysorbates and mono- and diacetyl glycerides, and mixtures thereof.

Its function is to lower the glass transition temperature of the coating film and to improve its mechanical properties.

It is used in a proportion of up to 40% and preferably between 15% and 30%, expressed on a weight basis relative to the dry weight of polymer.

The surfactant is chosen from anionic, cationic, nonionic and amphoteric surfactants.

The antistatic agent optionally used is employed to avoid problems associated with static electricity. It is chosen from the group comprising micronized or nonmicronized talc, colloidal silica (Aerosil® 200), treated silica (Aerosol® R972) and precipitated silica (Syloid® FP244), and mixtures thereof.

It is used in a proportion of up to 10% by weight, preferably between 0% and 3% and even more preferably less than 1% by weight.

The lubricant is chosen from the group comprising magnesium stearate, stearic acid, sodium stearyl fumarate, micronized polyoxyethylene glycols (micronized Macrogol 6000) and sodium benzoate, and mixtures thereof.

An optional polymer layer may be applied between the core and the functional polymer film to insulate the core, comprising the active principle, from the layer of cellulose-based polymer that allows the sustained release of the active principle.

The polymer constituting the optional layer may be chosen from the same polymers as those used as binder; in particular, it may be identical to or different than the polymer used as binder in the core comprising the active principle.

The advantage provided by this optional layer is that it allows the active principle to be insulated from the functional polymer that allows its sustained release,
  when there is incompatibility between the active principle and the functional polymer,
  when the active principle is unstable at the pH of the solution or suspension used to apply the functional polymer,
  when the active principle has a high solubility in the solvent used to apply the functional polymer, which may be the cause of "migration" of the active principle into the polymer film, thus making it difficult to obtain sustained release of the active principle.

The amount of polymer applied is between 1% and 10% and preferably between 2% and 5% as weight gain relative to the mass of cores comprising the active principle used.

In accordance with the invention, the layer of cellulose-based polymer allowing the sustained release of the active principle is covered with a coating that protects it.

This protective coating is based on at least one thermoplastic agent with a melting point of from about 25° C. to about 100° C. and optionally a lubricant.

The thermoplastic agent is chosen from the group comprising partially hydrogenated oils, beeswax, carnauba wax, paraffin waxes, silicone waxes, fatty alcohols, $C_{12}$-$C_{18}$ fatty acids, solid semisynthetic glycerides, glyceryl monoesters, diesters or triesters, polyoxyethylene glycols and polyoxyethylenated glycosyl glycerides, and mixtures thereof.

The function of the protective coating is to absorb the stresses caused by tabletting, and to avoid deformation, alteration or breaking of the coating film consisting of the cellulose-based polymer, the function of which is to ensure the sustained release of the active principle.

The thermoplastic agent is used in a proportion that may be up to 100% as weight gain and preferably between 10% and 50% as weight gain, relative to the mass of granulate to be coated.

It is preferably chosen from hydrophilic excipients with a hydrophilic/lipophilic balance (HLB) of greater than 10, so as not to modify the release profile of the active principle.

The protective coating may also comprise an antistatic agent.

The particle size distribution of the particles in accordance with the invention allows their use in the manufacture of multiparticulate tablets.

Advantageously, the size of the particles is less than 700 μm, given that the size of at least 50% and preferably of at least 70% of the particles is between 150 and 500 μm, and that the size of less than 15% of the particles is less than 150 μm.

The particle size is determined by the conventional methods, for example using a set of screens of calibrated mesh size, or by laser diffraction.

By virtue of their mechanical properties, the sustained-release coated particles thus prepared are particularly suitable for inclusion in the constitution of multiparticulate tablets.

The multiparticulate tablet in accordance with the invention is characterized in that it is based on coated particles in accordance with the invention, this tablet also comprising a mixture of excipients comprising
    a disintegrant and/or a swelling agent,
    at least one diluent,
    a lubricant, and
    optionally, an antistatic agent, a permeabilizer, sweeteners, flavorings and colorants.

The disintegrant is chosen from the group comprising crosslinked sodium carboxymethylcellulose, referred to in the art as croscarmellose, crospovidone and mixtures thereof.

The swelling agent is chosen from the group comprising microcrystalline cellulose, starches and modified starches.

The diluent may be chosen from the group comprising cellulose derivatives and preferentially microcrystalline cellulose, lactose and polyols, and preferentially mannitol.

The lubricant is chosen from the group comprising magnesium stearate, stearic acid, sodium stearyl fumarate, polyoxyethylene glycols (micronized Macrogol 6000) and sodium benzoate, and mixtures thereof.

The lubricant is totally or partially dispersed in the mixture of tabletting excipients and/or sprayed onto the surface of the tablet at the time of tabletting.

The antistatic agent may chosen from the group comprising colloidal silica, especially the product sold under the brand name Aerosil®, and preferentially precipitated silica, especially the product sold under the name Syloid® FP244, and micronized or nonmicronized talc, and mixtures thereof.

The permeabilizer is chosen from the group especially comprising silicas with great affinity for aqueous solvents, such as the precipitated silica more commonly known under the brand name Syloid®, maltodextrins and β-cyclodextrins, and mixtures thereof.

It allows the creation of a hydrophilic network that facilitates the penetration of saliva and thus contributes toward better disintegration of the tablet.

The sweetener may be chosen from the group especially comprising aspartame, potassium acesulfame, sodium saccharinate, neohesperidine dihydrochalcone, sucralose and monoammonium glycyrrhizinate, and mixtures thereof.

The flavorings and colorants are those usually used in pharmaceuticals for the preparation of tablets.

In the multiparticulate tablets in accordance with the invention, the proportion of the mixture of excipients relative to the coated particles is from 0.4 to 10 and preferably between 1 and 5 parts by weight, said mixture of excipients comprising:
    from 1% to 15% and preferably from 2% to 7% by weight of disintegrant and/or swelling agent,
    from 30% to 90% and preferably from 40% to 70% by weight, relative to the mass of the tablet, of diluent,
    from 0.02% to 2% and preferably from 0.5% to 1% by weight, relative to the mass of the tablet, of lubricant,
    from 0.5% to 5% by weight, relative to the mass of the tablet, of permeabilizer.

In one preferred embodiment, the multiparticulate tablet according to the invention is an orodispersible tablet that disintegrates in the mouth, on contact with the saliva, in less than 60 seconds and preferably in less than 40 seconds, forming a suspension that is easy to swallow.

The disintegration time corresponds to the duration between the moment that the tablet is placed in the mouth in contact with the saliva and the moment of swallowing of the suspension resulting from the disintegration without chewing of the tablet in contact with the saliva.

The diluent is chosen from soluble agents with binding properties, consisting of polyols of less than 13 carbon atoms and being either in the form of a directly compressible product with a mean particle diameter of from 100 to 500 μm, or in the form of a powder with a mean particle diameter of less than 100 μm, these polyols preferably being chosen from the group comprising mannitol, xylitol, sorbitol and maltitol, used in the form of a directly compressible product, whereas, in the case where there are at least two soluble diluents with binding properties, one is present in the directly compressible form and the other in the form of a powder, the polyol possibly being the same, the proportions of directly compressible polyol and of polyol powder being from 99/1 to 20/80 and preferably from 80/20 to 20/80.

A subject of the invention is also a process for preparing sustained-release coated particles.

The process under consideration comprises, in accordance with the invention, the following steps:
    preparation by wet granulation or mounting on neutral supports, of a core comprising the active principle,
    coating of the cores thus obtained by spraying a coating composition consisting of at least one cellulose-based polymer,
    coating of the coated particles thus obtained by spraying with a protective coating composition based on an excipient of thermoplastic type,
    drying.

According to this embodiment, the successive steps of the process may be performed in different machines or in the same machine.

In a first advantageous embodiment, the cores comprising the active principle are prepared by granulation according to the following steps:
    dry-mixing of the active principle in the form of powder or microcrystals, optionally with the diluent and an antistatic agent, granulation of the mixture obtained by spraying with a solution of the binder, drying.

For the granulation, a high-energy granulator, a planetary mixer or a fluidized air bed is advantageously used.

In the case of granulation in a fluidized air bed, the powder mixture containing the active principle and, possibly, the diluent and the antistatic agent, is introduced into the machine and then granulated by spraying onto said powder mixture a solution or suspension of excipients comprising at least one binder.

According to another advantageous embodiment, the polymer used during the granulation step and the polymer used during the coating step are identical. In this case, the granulation step differs from the coating step by different parameters, such as the spraying flow rate of the excipient mixture and the atomization pressure of said mixture.

Thus, during the granulation step, the spraying flow rate of excipient suspension is higher than during the coating step, whereas the atomization pressure of the excipient suspension is lower during the granulation step than during the coating step.

In practice, at the laboratory scale in a fluidized air bed machine, for example of the Glatt CPCG3 type, the spraying flow rate of the excipient mixture is, during the granulation step, from 15 to 30 grams/minute and the atomization pressure is from 1 to 2.5 bar.

During the coating step, the spraying flow rate of the coating suspension is from 10 to 25 grams/minute, while the atomization pressure is from 1.5 to 3 bar.

Advantageously, a proportion of from 10% to 30% of the mixture of excipients is sprayed during the granulation step, the remainder to 100% being sprayed during the coating step.

In a second embodiment of the cores comprising the active principle, they are prepared by mounting on neutral supports according to the following steps:

spraying onto neutral supports a solution or a suspension of the active principle, containing the dissolved binder, drying.

The cores thus obtained are then coated by successive spraying of the various coating compositions, and then dried.

The polymer coating consisting of a cellulose-based derivative is sprayed in the form of a solution, a suspension or a colloidal dispersion.

The thermoplastic excipient may be applied by spraying in the form of a solution in an aqueous or organic solvent.

In one particular embodiment, the thermoplastic excipient may be heated to a temperature above its melting point, and then sprayed in liquid form without solvent.

In this case, a thermostatically regulated spraying device that makes it possible to avoid obstructing the tubes is installed.

All the steps of the process in accordance with the invention may be performed in a sugar-coating turbomixer, in a perforated turbomixer or in a fluidized air bed.

In one preferred embodiment of the process in accordance with the invention, all the steps of preparation of the active core and of coating are performed in a fluidized air bed.

The fluidized air bed is equipped with a spraying nozzle whose spraying position and orientation may be chosen. The spraying is designated by the terms of the art "top spray", "bottom spray" or "tangential spray".

This choice makes it possible to control the growth kinetics of the particles and to avoid phenomena of adhesion, associated with the nature of the active principle and with the composition of the sprayed binder or coating composition, and various process parameters (for example temperature, air pressure or flow rate of solution).

The invention also relates to a process for preparing multiparticulate tablets comprising the sustained-release coated particles.

This process includes, in accordance with the invention, the following steps:

dry-mixing of the coated particles, obtained according to the process described above, with the tabletting excipients, compression of the mixture thus obtained, to make a unit form.

The compression of the mixture may be performed on an alternating or rotary tabletting machine.

The stresses exerted during the compression step may range from 5 kN to 50 kN and preferably from 5 kN to 15 kN.

The hardness of the tablets thus obtained is preferably from 1 to 10 kp and more preferably from 1 to 5 kp, measured according to the method of the European Pharmacopea (2.9.8), 1 kp being equal to 9.8 N.

Preferably, the hardness of the multiparticulate tablet is adapted firstly so as to obtain a friability of less than 2%, measured according to the method of the European Pharmacopea, while at the same time maintaining a dissolution profile identical to that of the coated particles, and secondly so as to obtain a disintegration time in the mouth of less than or equal to 60 seconds and preferably less than or equal to 40 seconds.

The tablets may have a diameter of from 6 mm to 17 mm. They may be round, oval or oblong in shape, having a flat or concave surface, and may optionally be engraved.

In the case of orodispersible tablets, "polo" punches may be used, i.e. punches for obtaining round, flat tablets with concavity at the center of the two faces.

The tablets have a mass preferably of between 0.1 and 2.0 grams.

The invention will be understood more clearly with the aid of the examples of preparation of the coated particles and of the multiparticulate tablets in accordance with the invention. These examples are given solely as illustrations and advantageous embodiments of the invention and do not in any way constitute a limitation thereof.

EXAMPLE 1

Coated granulates comprising oxycodone HCl as active principle.

Granulation 500 grams of oxycodone HCl are mixed with 15 grams of Syloid® 244 FP [i.e. 3% (w/w) relative to the mass of oxycodone HCl].

The mixture of powders is granulated in a planetary mixer using a wetting solution consisting of ethylcellulose N7, at a concentration of 8% (w/w) in isopropanol.

The grain formed is oven-dried at 45° C. for 5 hours and then screened through a 0.9 mm diameter screen.

Coating

The coating operation is performed in a Glatt GPCG-3 fluidized air bed equipped with a Würster insert ("bottom spray").

The mass obtained is spray-coated with the same solution as in the preceding step.

An amount of polymer corresponding to 42% (w/w), calculated as weight gain relative to the mass of starting uncoated granulates, is applied.

The particle size distribution of the coated particles E1 is given in Table 1.

TABLE 1

| Mesh aperture | E1 |
|---|---|
| >0.710 mm | 20.7% |
| 0.600 mm–0.710 mm | 11.5% |
| 0.500 mm–0.600 mm | 12.5% |
| 0.355 mm–0.500 mm | 17.4% |
| 0.180 mm–0.355 mm | 25.8% |
| 0.075 mm–0.180 mm | 7.9% |
| <0.075 mm | 4.2% |

The yield by mass is 96.32% (w/w). The composition of the coated granulates E1 is given in Table 2:

TABLE 2

|  | % (w/w) |
|---|---|
| Oxycodone HCl | 65.46 |
| Syloid ® 244FP | 1.96 |
| Ethylcellulose N7 | 32.60 |
| Isopropyl alcohol | — |

EXAMPLE 2

Orodispersible multiparticulate tablets comprising oxycodone HCl as active principle.

Compression

A "Manesty F3 press" alternating tabletting machine equipped with 8 mm diameter Polo punches is used.

The coated granulates obtained according to example 1 are mixed with tabletting excipients.

Two types of tablet are prepared, T1 and T2, respectively, comprising different relative proportions of coated oxycodone HCl granulates.

The tablets T1 and T2 have respective doses of 19.8 and 10 mg of oxycodone HCl, according to the indications of Table 3:

TABLE 3

| Constituents | T1 % by weight | T2 % by weight |
|---|---|---|
| Oxycodone HCl-coated granulates | 19.8 | 10.0 |
| Mannitol 300 | 33.2 | 37.3 |
| Mannitol 60 | 33.2 | 37.3 |
| Crospovidone | 9.8 | 10.0 |
| Orange flavoring | 1.0 | 1.0 |
| Syloid ® 244FP | 1.0 | 0.4 |
| Magnesium stearate | 2.0 | 2.0 |
| Aspartame | — | 2 |
| Total | 100 | 100 |

The tablets T1 and T2 have the characteristics indicated in Table 4:

TABLE 4

|  | T1 | T2 |
|---|---|---|
| Theoretical proportion granulates/tablet | 20% | 10% |
| Weight (mg) | 156.0 | 308.6 |
| Hardness (kP) | 1.5 | 1.5 |
| Friability | not determined | not determined |
| Disintegration time in the mouth | 10-15 sec | 15 sec |

A comparative dissolution profile between the coated granulates of example 1 (designated as E1) and the tablets of formulae T1 and T2 are established under the following conditions:
apparatus: USP type II
paddle speed: 100 rpm
volume: 900 ml
temperature: 37.0° C.±0.5° C.
detection: direct UV spectrophotometry at 244 nm
dissolution medium: 0.01 N HCl (pH=2).
The recorded results are collated in Table 5:

TABLE 5

| | Oxycodone released (% (w/w)) | | |
|---|---|---|---|
| Time (hours) | E1 | T1 | T2 |
| 0.5 | 16 | 37 | 43 |
| 1 | 30 | 53 | 58 |
| 2 | 47 | 74 | 78 |
| 4 | 69 | 92 | 95 |
| 6 | 78 | 95 | 98 |
| 8 | 81 | 96 | 99 |
| 10 | 81 | 96 | 99 |

Conclusion:

It is possible to deduce from the results collated in Table 5 that the compression causes rupture of the ethylcellulose film, which results in accelerated release of the active principle.

The result of this is that the mechanical properties of the coating film are not suitable for compression in the form of a sustained-release orodispersible tablet.

EXAMPLE 3

Coated granules comprising theophylline as active principle.

Mounting on Neutral Supports

The operation is performed in a Glatt GPCG-3 fluidized air bed equipped with a Würster insert ("bottom spray").

1500 grams of theophylline are suspended in 4500 g of isopropanol, into which have been predissolved 262.5 grams of PVP K29, i.e. polyvinylpyrrolidone or povidone, K29, the K value expressing the mean molecular weight of the povidones calculated from the relative viscosity in water and defined in the European Pharmacopea (section 2.2.1.2 and 2.3.2.1), used as binder [i.e. 17% (w/w) relative to the mass of theophylline].

1500 grams of neutral supports consisting of starch and sucrose, of about 250-350 μm in size, are introduced into the fluidized air bed.

Said alcoholic suspension containing the theophylline is sprayed onto the neutral supports.

Coating with Ethylcellulose N7

The operation is performed in a Glatt GPCG-3 fluidized air bed equipped with a Würster insert ("bottom spray").

600 grams of granules obtained in the preceding step are spray-coated with a solution of ethylcellulose N7 in isopropyl alcohol as prepared in example 1, also containing micronized talc, corresponding to 10% (w/w), relative to the dry mass of polymer.

An amount of polymer corresponding to 5% (w/w), calculated as weight gain relative to the mass of granules to be coated, is applied.

The particle size distribution of the coated particles obtained and designated by E2 is given in Table 6:

TABLE 6

| Mesh aperture | E2 |
| --- | --- |
| >0.500 mm | 6.6% |
| 0.425 mm-0.500 mm | 46.2% |
| 0.355 mm-0.425 mm | 38.2% |
| 0.250 mm-0.355 mm | 9.0% |

Protective Overcoating

The operation is performed in a Glatt GPCG-3 fluidized air bed equipped with a Würster insert ("bottom spray").

The coated granules E2 obtained in the preceding step are spray-coated with an aqueous solution of PEG 4000 also containing micronized talc corresponding to 10% (w/w), relative to the dry mass of PEG.

The protective coating is applied in an amount corresponding to 20% (w/w), calculated as weight gain relative to the mass of granules E2.

The particle size distribution of the coated particles E3 obtained by applying the protective coating to the granules E2 is given in Table 7:

TABLE 7

| Mesh aperture | E3 |
| --- | --- |
| >0.500 mm | 15.8% |
| 0.425 mm-0.500 mm | 41.2% |
| 0.355 mm-0.425 mm | 38.4% |
| 0.250 mm-0.355 mm | 4.6% |

A comparative dissolution profile between the coated granules E2 and E3 is established under the following conditions:
  apparatus: USP type II
  paddle speed: 100 rpm
  volume: 900 ml
  temperature: 37.0° C.±0.5° C.
  detection: direct UV spectrophotometry at 272 nm
  dissolution medium: 0.01 N HCl (pH=2).

The recorded results are collated in Table 8:

TABLE 8

| | Theophylline released (% (w/w)) | |
| --- | --- | --- |
| Time (hours) | E2 | E3 |
| 1 | 12 | 10 |
| 2 | 21 | 16 |
| 4 | 36 | 34 |
| 6 | 48 | 49 |
| 8 | 57 | 60 |
| 10 | 63 | 68 |

Conclusion

From the examination of the results collated in Table 8, it is seen that the application of the protective coating to the coated granules E2 does not significantly modify their dissolution profile.

EXAMPLE 4

Orodispersible tablets comprising theophylline as active principle.

Compression

A "Manesty F3 press" alternating tabletting machine equipped with 12 mm diameter Polo punches is used. The coated granules obtained according to example 3 are mixed with tabletting excipients, according to the two compositions indicated in Table 9, giving tablets T3 and T4 after compression.

TABLE 9

| Constituents | T3 % by weight | T4 % by weight |
| --- | --- | --- |
| Theophylline-coated granules E2 or E3 | 35 | 35 |
| Mannitol 300 | 26.5 | 26.5 |
| Mannitol 60 | 26.5 | 26.5 |
| Crospovidone | 10.0 | 10.0 |
| Flavoring | — | — |
| Syloid ® 244FP | 0.5 | 0.5 |
| Magnesium stearate | 1.0 | 1.0 |
| Aspartame | — | — |

The characteristics of the orodispersible multiparticulate tablets T3 and T4 are given in Table 10:

TABLE 10

| Characteristics | T3 | T4 |
| --- | --- | --- |
| Dose of active substance of the tablet (mg) | 80 | 70 |
| Tablet weight (mg) | 588.0 | 622.0 |
| Hardness (kP) | 3.8 | 3.1 |
| Friability (%) | 5.6 | 0.5 |
| Disintegration time in the mouth (seconds) | 29 | 35 |

A comparative dissolution profile under the conditions of example 3 is established between the multiparticulate orodispersible tablets T3 and T4 containing, respectively, the coated granules E2 and E3.

The recorded results are collated in Table 11:

TABLE 11

| | Theophylline released (% (w/w)) | |
| --- | --- | --- |
| Time (hours) | T3 (E2) | T4 (E3) |
| 1 | 51 (12) | 16 (10) |
| 2 | 67 (21) | 24 (16) |
| 4 | 83 (36) | 43 (34) |
| 6 | 91 (48) | 55 (49) |
| 8 | 95 (57) | 63 (60) |
| 10 | 98 (63) | 69 (68) |

Conclusion

Examination of the results collated in Table 11 makes it possible to deduce that the protective coating significantly improves the mechanical properties of the ethylcellulose N7 film in terms of compressive strength.

EXAMPLE 5

Orodispersible tablets comprising theophylline as active principle are prepared.

Compression

A "Manesty F3 press" alternating tabletting machine equipped with 12 mm diameter Polo punches is used. The coated granules E3 obtained according to example 3 are mixed with tabletting excipients according to the indications of Table 12, giving multiparticulate tablets designated as T5:

TABLE 12

| Constituents | T5 % by weight |
|---|---|
| Theophylline-coated granules E3 | 20 |
| Mannitol 300 | 32.8 |
| Mannitol 60 | 32.8 |
| Crospovidone | 10.0 |
| Flavoring | 1.0 |
| Syloid ® 244FP | 0.5 |
| Magnesium stearate | 1.0 |
| Aspartame | 2.0 |

The orodispersible multiparticulate tablets T5 have the characteristics resulting from Table 13:

TABLE 13

| | T5 |
|---|---|
| Dose of active substance of the tablet (mg) | 25 mg |
| Weight (mg) | 555.0 |
| Hardness (kP) | 2.5 |
| Friability (%) | 0.6 |
| Disintegration time in the mouth (seconds) | 26 |

The comparative dissolution profile under the conditions of example 3 is established between the coated granules E3 and the orodispersible multiparticulate tablets T5 containing said coated granules.

The recorded results are collated in Table 14:

TABLE 14

| Time (hours) | Theophylline released (% (w/w)) T5 (E3) |
|---|---|
| 1 | 21 (12) |
| 2 | 30 (21) |
| 4 | 43 (36) |
| 6 | 52 (48) |
| 8 | 60 (57) |
| 10 | 65 (63) |

A comparative dissolution profile of the orodispersible multiparticulate tablets T5 is established in various dissolution media, with respective pH values of 1.2, 4.5 and 6.8:

The recorded results are collated in Table 15:

TABLE 15

| Time | Theophylline released (% (w/w)) | | |
|---|---|---|---|
| (hours) | pH 1.2 | pH 4.5 | pH 6.8 |
| 1 | (21) | 21 | 22 |
| 2 | (30) | 31 | 31 |
| 4 | (43) | 44 | 44 |
| 6 | (52) | 53 | 54 |
| 8 | (60) | 60 | 62 |
| 10 | (65) | 66 | 68 |

Conclusion

From examination of the results collated in Table 15, it is possible to conclude that the protective coating significantly improves the mechanical properties of the ethylcellulose N7 film in terms of compressive strength.

It is also possible to see that the profiles obtained are independent of the pH of the medium in which the dissolution is performed.

EXAMPLE 6

To evaluate the differences existing between the compressive strengths in the case of the cellulose-based polymers, on the one hand, and the acrylic polymers, on the other hand, the same test as in examples 3 and 4 is carried out, using as coating polymer a polyacrylate known under the brand name Eudragit® NE30D sold by Röhm.

Coating with Eudragit® NE30D

The operation is performed in a Glatt GPCG-3 fluidized air bed equipped with a Würster insert ("bottom spray").

750 grams of granules obtained after mounting on neutral supports of example 3 are spray-coated with an aqueous dispersion of Eudragit® NE30D, diluted to 20% (w/w), also containing micronized talc, in an amount corresponding to 10% (w/w), relative to the dry mass of polymer.

An amount of polymer corresponding to 5% (w/w), calculated as weight gain relative to the mass of granules to be coated, is applied.

After coating, an additional step of maturation of the film at 60° C. for 2 hours is performed.

Particles designated as E4 are thus obtained, the particle size distribution of which is given in Table 16:

TABLE 16

| Mesh aperture | E4 |
|---|---|
| >0.500 mm | 20.6% |
| 0.425 mm-0.500 mm | 46.2% |
| 0.355 mm-0.425 mm | 26.4% |
| 0.250 mm-0.355 mm | 6.8% |

Application of a Protective Coating

The operation is performed in a Glatt GPCG-3 fluidized air bed equipped with a Würster insert ("bottom spray").

The coated granules E4 obtained in the preceding step are spray-coated with an aqueous solution of PEG 4000 also containing micronized talc, in a proportion corresponding to 10% (w/w) relative to the dry mass of PEG.

An amount of protective coating corresponding to 20% (w/w), calculated as weight gain relative to the mass of granule E4, is applied.

Coated particles E5 are thus obtained, the particle size distribution of which is given in Table 17:

TABLE 17

| Mesh aperture | E5 |
|---|---|
| >0.600 mm | 4.2% |
| 0.500 mm-0.600 mm | 23.6% |
| 0.425 mm-0.500 mm | 43.2% |
| 0.355 mm-0.425 mm | 24.2% |
| 0.250 mm-0.355 mm | 4.8% |

A comparative dissolution profile is established between the coated granules E4 and E5 under the conditions of example 3.

The recorded results are collated in Table 18:

TABLE 18

| | Theophylline released (% (w/w)) | |
|---|---|---|
| Time (hours) | E4 | E5 |
| 1 | 34 | 40 |
| 2 | 49 | 57 |
| 4 | 66 | 74 |
| 6 | 75 | 84 |
| 8 | 81 | 90 |
| 10 | 86 | 94 |

Conclusion

From examination of the data collated in Table 18, it is seen that the application of a protective coating to the granules E4 does not significantly modify their dissolution profile.

EXAMPLE 7

Orodispersible multiparticulate tablets comprising theophylline as active principle Compression A "Manesty F3 press" alternating tabletting machine equipped with 12 mm diameter Polo punches is used. The coated granules E4 and E5 obtained according to example 6 are mixed with tabletting excipients according to the composition of Table 19, and tablets T6 and T7 corresponding, respectively, to the coated granulates E4 and E5 are obtained:

TABLE 19

| | T6 % by weight | T7 % by weight |
|---|---|---|
| Theophylline-coated granules | 35 | 35 |
| Mannitol 300 | 26.5 | 26.5 |
| Mannitol 60 | 26.5 | 26.5 |
| Crospovidone | 10.0 | 10.0 |
| Flavoring | — | — |
| Syloid ® 244FP | 0.5 | 0.5 |
| Magnesium stearate | 1.0 | 1.0 |
| Aspartame | — | — |

The characteristics of the tablets T6 and T7 are collated in Table 20:

TABLE 20

| | T6 | T7 |
|---|---|---|
| Dose of active substance of the tablet (mg) | 100 | 70 |
| Weight (mg) | 680.0 | 583.0 |
| Hardness (kP) | 4.2 | 3.3 |
| Friability (%) | 0.8 | 0.5 |
| Disintegration time in the mouth (seconds) | 14 | 35 |

A comparative dissolution profile is established under the conditions of example 3, between the multiparticulate orodispersible tablets T6 and T7, containing the coated granules E4 and E5, respectively. The recorded results are collated in Table 21:

TABLE 21

| | Theophylline released (% (w/w)) | |
|---|---|---|
| Time (hours) | T6 (E4) | T7 (E5) |
| 1 | 46 (34) | 48 (40) |
| 2 | 65 (49) | 66 (57) |
| 4 | 82 (66) | 83 (74) |
| 6 | 90 (75) | 92 (84) |
| 8 | 94 (81) | 98 (90) |
| 10 | 97 (86) | 100 (94) |

Conclusion

From examination of the data collated in Table 21, it is found that the protective coating does not improve the mechanical properties of the film formed with Eudragit® NE30D, which is already flexible and deformable. This is attested by the low variation observed between the dissolution profiles of the orodispersible tablets T6 and T7 containing the coated granules E4 and E5, respectively.

EXAMPLE 8

Compression

A "Manesty F3 press" alternating tabletting machine equipped with 12 mm diameter Polo punches is used. The coated granules E5 obtained according to example 6 are mixed with tabletting excipients according to the composition of Table 22, in which the multiparticulate tablets obtained are designated as T8:

TABLE 22

| | T8 % by weight |
|---|---|
| Theophylline-coated granules E5 | 20 |
| Mannitol 300 | 32.8 |
| Mannitol 60 | 32.8 |
| Crospovidone | 10.0 |
| Flavoring | 1.0 |
| Syloid ® 244FP | 0.5 |
| Magnesium stearate | 1.0 |
| Aspartame | 2.0 |

The characteristics of the orodispersible multiparticulate tablets T8 are collated in Table 23:

TABLE 23

|  | T8 |
| --- | --- |
| Dose of active substance of the tablet (mg) | 40 |
| Weight (mg) | 580.0 |
| Hardness (kP) | 2.7 |
| Friability (%) | 0.4 |
| Disintegration time in the mouth (seconds) | 27 |

A comparative dissolution profile is established under the conditions of example 3, between the coated granules E5 and the orodispersible tablets T8, containing said coated granules E5.

The recorded results are collated in Table 24:

TABLE 24

| Time (hours) | Theophylline released (% (w/w)) T8 (E5) |
| --- | --- |
| 1 | 45 (40) |
| 2 | 65 (57) |
| 4 | 85 (74) |
| 6 | 95 (84) |
| 8 | 100 (90) |
| 10 | 100 (94) |

A comparative dissolution profile of the orodispersible multiparticulate tablets T8 is moreover established in three dissolution media, of pH 1.2, 4.5 and 6.8, respectively.

The results are given in Table 25:

TABLE 25

| Time | Theophylline released (% (w/w)) | | |
| --- | --- | --- | --- |
| (hours) | pH 1.2 | pH 4.5 | pH 6.8 |
| 1 | (45) | 45 | 46 |
| 2 | (65) | 64 | 65 |
| 4 | (85) | 84 | 84 |
| 6 | (95) | 94 | 93 |
| 8 | (100) | 100 | 99 |
| 10 | (100) | 100 | 100 |

Conclusion

From examination of the results collated in Table 25, it is seen that the dissolution profile is not significantly modified by the compression and that the profiles obtained are independent of the pH of the medium in which the dissolution is performed.

The invention claimed is:

1. A multiparticulate tablet comprising sustained-release coated particles and a mixture of excipients, wherein said mixture of excipients comprises:
    a disintegrant and/or swelling agent,
    at least one diluent, and
    a lubricant,
and said sustained-release coated particles comprise:
    a core comprising at least one active principle and at least one binder,
    a coating film consisting of ethylcellulose which ensures sustained release of the active principle and none, one or more of a pore-forming agent, a surfactant, an antistatic agent and a lubricant, and
    at least one thermoplastic agent which is applied as a protective coating onto the coating film, wherein said thermoplastic agent is selected from the group consisting of partially hydrogenated oils, beeswax, carnauba wax, paraffin waxes, silicone waxes, fatty alcohols, $C_{12}$-$C_{18}$ fatty acids, solid semisynthetic glycerides, glyceryl monoesters, diesters or triesters, polyoxyethylene glycols, polyoxyethylenated glycosyl glycerides, and mixtures thereof, and wherein said thermoplastic agent has a melting point of from about 25° C. to about 100° C.,
and wherein a proportion of the mixture of excipients relative to the coated particles is from 1 to 5 parts by weight.

2. The multiparticulate tablet of claim 1, wherein said thermoplastic agent has a hydrophilic/lipophilic balance (HLB) greater than 10.

3. The multiparticulate tablet of claim 1, wherein the mixture of excipients further comprises an additional excipient selected from the group consisting of a binder, a permeabilizer, sweeteners, flavorings, colorants and mixtures thereof, and wherein the protective coating further comprises an antistatic agent and a lubricant.

4. The multiparticulate tablet of claim 1, wherein the tablet is adapted to disintegrate in a mouth on contact with saliva in less than 60 seconds, forming a suspension that is easy to swallow.

5. A multiparticulate tablet comprising sustained-release coated particles and a mixture of excipients, wherein said mixture of excipients comprises:
    at least one disintegrant,
    at least one diluent,
    a lubricant, and optionally a swelling agent, a permeabilizer, sweeteners, and flavorings,
and said sustained-release coated particles comprise:
    a core comprising at least one active principle and at least one binder,
    a coating film consisting of ethylcellulose which ensures sustained release of the active principle and none, one or more of a pore-forming agent, a surfactant, an antistatic agent and a lubricant, and
    at least one thermoplastic agent which is applied as a protective coating onto the coating film, wherein said thermoplastic agent is selected from the group consisting of partially hydrogenated oils, beeswax, carnauba wax, paraffin waxes, silicone waxes, fatty alcohols, $C_{12}$-$C_{18}$ fatty acids, solid semisynthetic glycerides, glyceryl monoesters, diesters or triesters, polyoxyethylene glycols and polyoxyethylenated glycosyl glycerides, and mixtures thereof, and wherein said thermoplastic agent has a melting point of from about 25° C. to about 100° C.,
wherein the multiparticulate tablet is adapted to disintegrate in a mouth on contact with saliva in less than 60 seconds, forming a suspension that is easy to swallow, and wherein a proportion of the mixture of excipients relative to the coated particles is from 1 to 5 parts by weight.

6. The multiparticulate tablet of claim 5, wherein the at least one diluent is chosen from soluble agents with binding properties, consisting of a polyol of less than 13 carbon atoms and being in the form of a directly compressible product with a mean particle diameter of from 100 to 500 μm, or in the form of a powder with a mean particle diameter of less than 100 μm, this polyol being a member selected from the group consisting of mannitol, xylitol, sorbital and maltitol.

7. The multiparticulate tablet of claim 1, wherein the at least one active principle is selected from the group consisting of gastrointestinal sedatives, antacids, analgesics, antiinflammatories, coronary vasodilators, peripheral and cerebral vasodilators, antiinfectives, antibiotics, antiviral agents, antiparasitic agents, anticancer agents, anxiolytics, neuroleptics, central nervous system stimulants, antidepressants, antihistamines, antidiarrheal agents, laxatives, dietary supplements, immunodepressants, hypocholesterolemiants, hormones, enzymes, antispasmodics, antianginal agents, medicinal products that decrease the heart rate, medicinal products that regulate the heart rate, medicinal products used in the treatment of arterial hypertension, antimigraine agents, medicinal products that decrease blood clotting, medicinal products that increase blood clotting, antiepileptics, muscle relaxants, medicinal products used in the treatment of diabetes, medicinal products used in the treatment of thyroid dysfunctions, diuretics, anorexigenic agents, antiasthmatics, expectorants, antitussive agents, mucoregulators, decongestants, hypnotics, antinausea agents, hematopoietic agents, uricosuric agents, plant extracts and contrast agents.

8. The multiparticulate tablet of claim 1, wherein the binder of the sustained-release coated particles is a member selected from the group consisting of cellulosic polymers, acrylic polymers, povidones, copovidones, polyvinyl alcohols, alginic acid, sodium alginate, starch, pregelatinized starch, sugars and derivatives thereof, guar gum and polyethylene glycols, and mixtures thereof.

9. The multiparticulate tablet of claim 1, wherein:
the core of the sustained-release coated particles further comprises a diluent and an antistatic agent, and
a polymer layer is applied between the core and the coating film of the sustained-release coated particles.

10. The multiparticulate tablet of claim 1, wherein the diameter of the sustained-release coated particles is from 150 to 700 μm with at least 50% of the particles having a diameter from 150 to 500 μm, and less than 15% of the particles having a diameter of less than 150 μm.

11. A method for preparing the sustained-release coated particles of the multiparticulate tablet of claim 1, the method comprising:
(a) preparing by wet granulation or mounting on neutral supports, cores comprising at least one active principle,
(b) coating the cores thus obtained by spraying a coating composition consisting of ethylcellulose which ensures sustained release of the active principle and none, one or more of a pore-forming agent, a surfactant, an antistatic agent and a lubricant to obtain coated cores,
(c) coating the coated cores thus obtained by spraying with a protective coating composition comprising a thermoplastic agent, dissolved in an aqueous solvent devoid of organic solvent, and
(d) drying.

12. A multiparticulate tablet comprising sustained-release coated particles and a mixture of excipients, wherein said mixture of excipients comprises:
a disintegrant and/or swelling agent,
at least one diluent,
a lubricant, and
an antistatic agent, a permeabilizer, sweeteners, flavorings and colorants,
and said sustained-release coated particles comprise:
a core comprising at least one active principle and at least one binder,
a coating film consisting of ethylcellulose which ensures sustained release of the active principle and none, one or more of a pore-forming agent, a surfactant, an antistatic agent and a lubricant, and
at least one thermoplastic agent which is applied as a protective coating onto the coating film, wherein said thermoplastic agent is selected from the group consisting of partially hydrogenated oils, beeswax, carnauba wax, paraffin waxes, silicone waxes, fatty alcohols, $C_{12}$-$C_{18}$ fatty acids, solid semisynthetic glycerides, glyceryl monoesters, diesters or triesters, polyoxyethylene glycols and polyoxyethylenated glycosyl glycerides, and mixtures thereof, and wherein said thermoplastic agent has a melting point of from about 25° C. to about 100° C.,
and wherein a proportion of the mixture of excipients relative to the coated particles is from 1 to 5 parts by weight.

13. The multiparticulate tablet of claim 12, wherein said thermoplastic agent has a hydrophilic/lipophilic balance (HLB) greater than 10.

14. The multiparticulate tablet of claim 1, further comprising a binder, a permeabilizer, sweeteners, flavorings and colorants and wherein the protective coating of the sustained-release coated particles further comprises an antistatic agent and a lubricant.

15. The multiparticulate tablet of claim 12, wherein the tablet is adapted to disintegrate in a mouth on contact with saliva in less than 60 seconds, forming a suspension that is easy to swallow.

16. The multiparticulate tablet of claim 12, wherein the at least one diluent is selected from soluble agents with binding properties, consisting of a polyol of less than 13 carbon atoms and being in the form of a directly compressible product with a mean particle diameter of from 100 to 500 μm, or in the form of a powder with a mean particle diameter of less than 100 μm, this polyol being selected from the group consisting of mannitol, xylitol, sorbitol and maltitol.

17. The multiparticulate tablet of claim 12, wherein the at least one active principle is selected from the group consisting of gastrointestinal sedatives, antacids, analgesics, antiinflammatories, coronary vasodilators, peripheral and cerebral vasodilators, antiinfectives, antibiotics, antiviral agents, antiparasitic agents, anticancer agents, anxiolytics, neuroleptics, central nervous system stimulants, antidepressants, antihistamines, antidiarrheal agents, laxatives, dietary supplements, immunodepressants, hypocholesteroleminats, hormones, enzymes, antispasmodics, antianginal agents, medicinal products that decrease the heart rate, medicinal products that regulate the heart rate, medicinal products used in the treatment of arterial hypertension, antimigraine agents, medicinal products that increase blood clotting, medicinal products that decrease blood clotting, antiepileptics, muscle relaxants, medicinal products used in the treatment of diabetes, medicinal products used in the treatment of thyroid dysfunctions, diuretics, anorexigenic agents, antiasthmatics, expectorants, antitussive agents, muco-regulators, decongestants, hypnotics, antinausea agents, hematopoietic agents, uricosuric agents, plant extracts and constrast agents.

18. The multiparticulate tablet of claim 14, wherein the binder of the sustained-release coated particles is selected from the group consisting of cellulosic polymers, acrylic polymers, povidones, copovidones, polyvinyl alcohols, alginic acid, sodium alginate, starch, pregelatinized starch, sugars and derivatives thereof, guar gum and polyethylene glycols, and mixtures thereof.

19. The multiparticulate tablet of claim 12, wherein:
the core of the sustained-release coated particles further comprises a diluent and an antistatic agent, and
a polymer layer is applied between the core and the coating film of the sustained-release coated particles.

20. The multiparticulate tablet of claim 12, wherein the diameter of the coated particles is from 150 to 700 μm, with at least 50% of the particles having a diameter from 150 to 500 μm, and less than 15% of the particles having a diameter of less than 150 μm.

21. A method for preparing the sustained-release coated particles of the multiparticulate tablet of claim 12, the method comprising:
(a) preparing by wet granulation or mounting on neutral supports, cores comprising at least one active principle,
b) coating the cores thus obtained by spraying a coating composition consisting of ethylcellulose which ensures sustained release of the active principle and none, one or more of a pore-forming agent, a surfactant, an antistatic agent and a lubricant to obtain coated cores,
(c) coating the coated cores thus obtained by spraying with a protective coating composition consisting of a thermoplastic agent, dissolved in an aqueous solvent devoid of organic solvent, and
(d) drying.

22. The multiparticulate tablet of claim 6, wherein the mixture of excipients comprises two diluents, wherein one of the diluents is in a form of a directly compressible product with a mean particle diameter from 100 to 500 μm, the other diluent is in a form of a powder with a mean particle diameter of less than 100 μm, and proportions of directly compressible product and of powder are from 99/1 to 20/80.

23. The multiparticulate tablet of claim 16, wherein the mixture of excipients comprises two diluents, wherein one of the diluents is in a form of a directly compressible product with a mean particle diameter from 100 to 500 μm, the other diluent is in a form of a powder with a mean particle diameter of less than 100 μm, and proportions of directly compressible product and of powder are from 99/1 to 20/80.

\* \* \* \* \*